(12) United States Patent
Demers et al.

(10) Patent No.: US 9,404,853 B1
(45) Date of Patent: *Aug. 2, 2016

(54) TERAHERTZ SPECTROMETER WITH PHASE MODULATION

(71) Applicant: Joseph R. Demers, Pasadena, CA (US)

(72) Inventors: Joseph R. Demers, Pasadena, CA (US); Bryon L. Kasper, Sierra Madre, CA (US)

(73) Assignee: Joseph R. Demers, Pasadena, CA (US)

( * ) Notice: Subject to any disclaimer, the term of this patent is extended or adjusted under 35 U.S.C. 154(b) by 81 days.

This patent is subject to a terminal disclaimer.

(21) Appl. No.: 14/262,291

(22) Filed: Apr. 25, 2014

(51) Int. Cl.
*G01J 5/02* (2006.01)
*G01N 21/3581* (2014.01)
*G01J 3/28* (2006.01)

(52) U.S. Cl.
CPC .............. *G01N 21/3581* (2013.01); *G01J 3/28* (2013.01)

(58) Field of Classification Search
CPC . G01N 21/35; G01N 21/359; G01N 21/3504; G01J 3/02; G01J 3/42
See application file for complete search history.

(56) References Cited

U.S. PATENT DOCUMENTS

| | | | |
|---|---|---|---|
| 4,594,511 | A | 6/1986 | Cooper et al. |
| 5,379,110 | A | 1/1995 | Matsui et al. |
| 5,379,309 | A | 1/1995 | Logan, Jr. |
| 5,623,145 | A | 4/1997 | Nuss |
| 6,304,219 | B1 | 10/2001 | Rothe et al. |
| 6,348,683 | B1 | 2/2002 | Verghese et al. |
| 6,434,496 | B1 | 8/2002 | Dong et al. |
| 6,545,785 | B1 | 4/2003 | Heflinger et al. |
| 6,811,552 | B2 | 11/2004 | Weil, Sr. et al. |
| 6,816,647 | B1 | 11/2004 | Rudd et al. |
| 6,828,558 | B1 | 12/2004 | Arnone et al. |
| 6,844,552 | B2 | 1/2005 | Zhang et al. |
| 6,849,852 | B2 | 2/2005 | Williamson |
| 6,865,014 | B2 | 3/2005 | Ciesla et al. |
| 6,957,099 | B1 | 10/2005 | Arnone et al. |
| 7,126,078 | B2 | 10/2006 | Demers et al. |
| 7,174,037 | B2 | 2/2007 | Arnone et al. |
| 7,244,934 | B2 | 7/2007 | Arnone et al. |
| 7,291,835 | B2 | 11/2007 | Overney |
| 7,291,839 | B1 | 11/2007 | Demers et al. |
| 7,335,883 | B2 | 2/2008 | Wallace et al. |
| 7,439,511 | B2 | 10/2008 | Demers |
| 7,485,863 | B2 | 2/2009 | Cole |
| 7,535,005 | B2 | 5/2009 | Demers |
| 7,781,736 | B2 | 8/2010 | Logan, Jr. et al. |

(Continued)

FOREIGN PATENT DOCUMENTS

| | | |
|---|---|---|
| EP | 1233527 | 8/2002 |
| GB | 2381121 | 4/2003 |

(Continued)

OTHER PUBLICATIONS

U.S. Appl. No. 14/183,088, filed Feb. 18, 2014, Demers et al.

(Continued)

*Primary Examiner* — David Porta
*Assistant Examiner* — Mamadou Faye
(74) *Attorney, Agent, or Firm* — Pritzkau Patent Group, LLC

(57) ABSTRACT

A highly advantageous terahertz spectrometer with phase modulation and associated method are disclosed which utilize a second harmonic for generating an error signal to control a phase modulator to at least reduce nulls of an interference pattern.

12 Claims, 7 Drawing Sheets

(56) References Cited

U.S. PATENT DOCUMENTS

| | | |
|---|---|---|
| 7,804,069 B2 | 9/2010 | Tribe |
| 7,936,453 B2 | 5/2011 | Logan, Jr. et al. |
| 7,963,571 B2 | 6/2011 | Martin |
| 8,138,477 B2 | 3/2012 | Gregory |
| 8,604,433 B2 | 12/2013 | Logan, Jr. et al. |
| 9,086,374 B1 * | 7/2015 | Demers et al. |
| 2003/0155512 A1 | 8/2003 | Arnone et al. |
| 2004/0065831 A1 | 4/2004 | Federici et al. |
| 2005/0162658 A1 | 7/2005 | Pepper |
| 2006/0084180 A1 | 4/2006 | Paldus et al. |
| 2006/0214107 A1 | 9/2006 | Mueller |
| 2006/0255277 A1 | 11/2006 | Cole et al. |
| 2008/0179519 A1 | 7/2008 | Andonian et al. |
| 2008/0179528 A1 | 7/2008 | Demers |
| 2008/0212974 A1 | 9/2008 | Davies et al. |
| 2008/0251720 A1 | 10/2008 | Xu et al. |
| 2009/0015843 A1 | 1/2009 | Demers et al. |
| 2009/0066948 A1 | 3/2009 | Karpowicz et al. |
| 2009/0091820 A1 | 4/2009 | McCarthy et al. |
| 2009/0180122 A1 | 7/2009 | Federici |
| 2009/0200472 A1 | 8/2009 | Gregory |
| 2009/0283680 A1 | 11/2009 | Logan, Jr. et al. |
| 2010/0080505 A1 | 4/2010 | Sartorius et al. |
| 2010/0092183 A1 | 4/2010 | Kim et al. |
| 2010/0148069 A1 * | 6/2010 | Ouchi ............... G01N 21/3581 250/341.8 |
| 2010/0171835 A1 | 7/2010 | Kasai et al. |
| 2011/0032955 A1 | 2/2011 | Daiber |
| 2011/0068268 A1 | 3/2011 | Heidari |
| 2012/0075477 A1 | 3/2012 | Daly et al. |
| 2012/0326039 A1 | 12/2012 | Demers et al. |
| 2013/0200263 A1 | 8/2013 | Logan et al. |
| 2014/0021351 A1 | 1/2014 | Logan et al. |
| 2014/0043612 A1 | 2/2014 | Logan, Jr. et al. |

FOREIGN PATENT DOCUMENTS

| | | |
|---|---|---|
| GB | 2483118 | 2/2012 |
| WO | WO 2007/135382 A2 | 11/2007 |
| WO | WO 2009/082820 A1 | 7/2009 |
| WO | WO 2009/137263 A2 | 11/2009 |
| WO | WO 2009/137263 A3 | 1/2010 |

OTHER PUBLICATIONS

Brown, "Advancements in Photomixing and Photoconductive Switching for THz Spectroscopy and Imaging," *Proc. of SPIE*, 2013; 7938:793802-1-793802-16.

Intellectual Property Office Search Report for Application No. GB10170462 dated Nov. 16, 2010; 1 page.

U.S. Appl. No. 61/054,344, filed May 19, 2008, Logan, Jr. et al.

U.S. Appl. No. 14/212,542, filed Mar. 14, 2014, Demers et al.

U.S. Appl. No. 14/262,249, filed Apr. 25, 2014, Demers et al.

Arnone et al., "Applications of Terahertz (THz) Technology to Medical Imaging," *Proc. SPIE Terahertz Spectroscopy Applicat. II*, 1999; 3823:209-219.

Arnone et al., "Terahertz Imaging Comes Into View," *Phys. World*, 2000; pp. 35-40.

Bartels et al., "Femtosecond Time-Resolved Optical Pump-Probe Spectroscopy at Kilo Rates Over Nanosecond-Time-Delays Without Mechanical Delay Line," *Appl. Phys. Lett.*, 2006; 88:04117.

Bartels et al., "High-Resolution THz Spectrometer with kHz Scan Rates," *Optics Express*, 2006; 14(1):430-437.

Bjanason et al., "ErAs:GaAs Photomixer with two decades tenability and 12 μW Peak Output," *Applied Physics Letters*, 2004; 85(18):3983-3985.

Brown et al., "Characterization of a Planar Self-Complementary Square-Spiral Antenna in the THz Region," *Microwave and Optical Technology Letters*, Mar. 2006; 48(3):524-529.

Chang et al., "Power Scalable Compact THz System Based on an Ultrafast Yb-doped Fiber Amplifier," *Optics Express*, 2006; 14(17):7909-7913.

Chen et al., "Spectroscopic Applications and Frequency Locking of THz Photomixing with Distributed-Bragg-Reflector Diode Lasers in Low-Temperature-Grown GaAs," *Appl. Phys. Lett.*, 1997; 71(12):1601-1603.

Combined Search and Examination Report for Application No. GB1309663.1 dated Nov. 13, 2013; 8 pgs.

Demers et al., "An Optically Integrated Coherent Frequency-Domain THz Spectrometer with Signal-to-Noise Ratio up to 80 dB," 2007 IEEE Conference; pp. 92-95.

Demers et al., "Field-portable THz Spectrometer for Characterization of Explosives and Chemicals," IEEE IRMMW Conference, Houston, TX, Oct. 6, 2011; 26 pgs.

Gutierrez, "An Electro-Optical Frequency Shifter," NASA's Jet Propulsion Laboratory, 2000; Available at <URL:http://www.nasatech.com/Briefs/Sept00/NPO20531.html>.

Hu et al., "Imaging with Terahertz Waves," *Optics Letters*, 1995; 20(16):1716-1718.

Hunsche et al., "Terahertz 'T-Ray' Tomography," *Proc. SPIE Int. Millimeter Submillimeter Waves Applicat. IV*, 1998; 50(3):426-433.

Izutsu et al., "Integrated Optical SSB Modulator/Frequency Shifter," *IEEE Journal of Quantum Electronics*, Nov. 1981, QE-17:2225-2227.

Janke et al., "Asynchronous Optical Sampling for High-Speed Characterization of Integrated Resonant Terahertz Sensors," *Optics Letters*, 2005; 30(11):1405-1407.

Jiang et al., "Terahertz Imaging via Eletrooptic Effect," *IEEE Trans. Microwave Theory Tech.*, 1999; 47:2644-2650.

Logan, Jr. et al., "Field Portable THz Spectrometer for Characterization of Explosives and Chemicals," Emcore Corporation Conference Publication, Oct. 2011; 3 pgs.

McGrath et al., "Superconductive Hot Electron Mixers with Ultra Wide RF Bandwidth for Heterodyne Receiver Applications Up to 3 THz," *Proceedings of the ESA Symposium*, 1997; pp. 401-404.

McIntosh et al., "Terahertz Measurements of Resonant Planar Antennas Coupled to Low-Temperature-Grown GaAs Photomixers," *Appl. Phys. Lett.*, 1996; 69(24):3632-3634.

Mittleman et al., "T-Ray Imaging," *IEEE J. Select. Topics Quantum Electron*, 1996; 2:679-692.

Saleh et al., "Fundamentals of Photonics," Wiley-Interscience, 1991; pp. 719-720, 823-825.

Siegel, "Terahertz Technology," *IEEE Transactions on Microwave Theory and Techniques*, 2002; 50(3):915-917.

Verghese et al., "Generation and Detection of Coherent Terahertz Waves Using Two Photomixers," *Applied Physics Letters*, 1998; 73(26):3824-3826.

Wu et al., "Two-Dimensional Electro-Optic Imaging of THz Beams," *Appl. Phys. Lett.*, 1996; 69(8):1026-1028.

Yasui et al., "Terahertz Frequency Comb by Multifrequency-Heterodyning Photoconductive Detection for Hig-Accuracy, High Resolution Terahertz Spectroscopy," *Applied Physics Letters*, 2006; 88(241104):1-3.

\* cited by examiner

TERAHERTZ SPECTROMETER WITH PHASE MODULATION

REFERENCE TO RELATED APPLICATIONS

The present invention is related to co-pending U.S. patent application Ser. No. 12/465,219 filed May 13, 2009, Ser. No. 12/861,651 filed Aug. 23, 2010, Ser. No. 13/565,021 filed Aug. 2, 2012, Ser. No. 14/212,542 filed Mar. 14, 2014, and Ser. No. 14/262,249 filed Apr. 25, 2014.

BACKGROUND

The present invention is related to terahertz spectroscopy and, more particularly, to an advanced apparatus, system and methods for employing terahertz frequency radiation for characterizing and/or detecting materials.

Electromagnetic radiation in the sub-millimeter and terahertz (THz) frequency ranges has been employed for characterizing molecular gases, including materials of atmospheric importance. Recently terahertz radiation has been utilized for the characterization and/or detection of solids as well as gases. Many different materials have distinct and measurable characteristic signatures in the terahertz frequency range. For example, these materials can absorb electromagnetic radiation at certain terahertz frequencies that are unique for a given material or materials and which can be used to identify the given material. Materials that exhibit these characteristics signatures include: illicit drugs, biologically important compounds such as sugars and hormones, and explosives. Terahertz radiation can also be used in the field of art conservation, for example, to determine the proper materials for restoring paintings.

Many dielectric, nonmetallic materials are transparent at terahertz frequencies which makes it is possible to measure or detect other materials that are hidden behind such terahertz transparent materials. Some examples of terahertz transparent materials include: fabrics, packaging materials, and paper. Also, in the case of art characterization, layers of paint are also transparent to terahertz frequency radiation. Nonpolar liquids are also transparent to terahertz radiation.

In addition, terahertz radiation is non-ionizing and is completely eye safe. Because of this, terahertz radiation can be used in public areas without the risk of harm to humans, flora, or fauna. This can be especially beneficial because people using the terahertz frequency radiation are not encumbered by unwieldy radiation protection such as is common, for example, when using x-rays.

The foregoing examples of the related art and limitations related therewith are intended to be illustrative and not exclusive. Other limitations of the related art will become apparent to those of skill in the art upon reading of the specification and a study of the drawings.

SUMMARY

The following embodiments and aspects thereof are described and illustrated in conjunction with systems, tools and methods which are meant to be exemplary and illustrative, not limiting in scope. In various embodiments, one or more of the above-described problems have been reduced or eliminated, while other embodiments are directed to other improvements.

In general, terahertz frequency spectrometers are described for identifying a terahertz frequency spectral characteristic of a material in a sampling region. In an embodiment, a terahertz frequency spectrometer includes a terahertz source for generating a first terahertz signal and for transmitting a terahertz electromagnetic radiation beam, based on the first terahertz signal, to the sampling region such that a characterized terahertz radiation is produced by an interaction of the terahertz electromagnetic radiation beam with the material in the sampling region. The characterized terahertz radiation includes the terahertz frequency spectral characteristic related to the material. A terahertz detector is included for generating a second terahertz signal and for receiving the characterized terahertz electromagnetic radiation from the sampling region and producing a characterized terahertz signal responsive to the receipt radiation. The terahertz detector is configured to mix the characterized terahertz signal and the second terahertz signal to produce a characterized detector signal. The phase modulator is included for applying a phase modulation and we modulate the phase of at least one of the first terahertz signal and second terahertz signal in a periodic manner at a modulating frequency. The phase modulator modulates the phase relative to a phase offset that is a difference between the faces of the characterized terahertz signal and the second terahertz signal. The characterized detector signal includes a characterized signal component that is related to the characteristic of the material, a first harmonic signal component in a first harmonic of the modulating frequency resulting from the phase modulation, and a second harmonic signal component at a second harmonic of the modulating frequency resulting, at least in part, from the phase offset. A characteristic detector is included for extracting the characterized signal component from the detector signal to identify the terahertz frequency spectral characteristic of the material in the sampling region. The extracted characterized signal component defines a characterized power curve that includes nulls which are reduced power levels at certain frequencies related to the second harmonic signal component of the detector signal. The phase offset controller is included for controlling the phase offset using the second harmonic signal component such that nulls are, at least in part, removed from the characterized power curve.

In another embodiment, a terahertz frequency spectrometer is disclosed for identifying a terahertz frequency spectral characteristic of a material in a sampling region. A terahertz beam source is included for generating a terahertz beam that passes through the sampling region thereby producing a characterized terahertz radiation as influenced by the material. A local oscillator generator is included for generating a terahertz local oscillator signal at the same frequency as the terahertz beam. A phase modulator is included for applying the phase modulation in a way that modulates the phase of at least one of the terahertz beam and terahertz local oscillator signal based on the modulation input. A mixer is included for producing an output signal based on the characterized terahertz radiation and the terahertz local oscillator signal that can exhibit a pattern of nulls resulting from the phase modulation and which includes a first harmonic that characterizes the terahertz spectral characteristic of the sample. A lock-in amplifier is included for detecting the second harmonic of the output signal to produce an error signal for driving the modulation input based on the error signal to at least reduce the nulls.

In addition to the exemplary aspects and embodiments described above, further aspects and embodiments will become apparent by reference to the drawings and by study of the following descriptions.

BRIEF DESCRIPTION OF THE DRAWINGS

FIG. 4b is an illustration of components of a detector signal which can result from the waveform of FIG. 4a.

FIG. 5b is an illustration of components of a detector signal which can result from the waveform of FIG. 5a.

DETAILED DESCRIPTION

The following description is presented to enable one of ordinary skill in the art to make and use the invention and is provided in the context of a patent application and its requirements. Various modifications to the described embodiments will be readily apparent to those skilled in the art and the generic principles taught herein may be applied to other embodiments. Thus, the present invention is not intended to be limited to the embodiments shown, but is to be accorded the widest scope consistent with the principles and features described herein including modifications and equivalents, as defined within the scope of the appended claims. It is noted that the drawings are not to scale and are diagrammatic in nature in a way that is thought to best illustrate features of interest. Descriptive terminology may be adopted for purposes of enhancing the reader's understanding, with respect to the various views provided in the Figures, and is in no way intended as being limiting.

Figure 1:
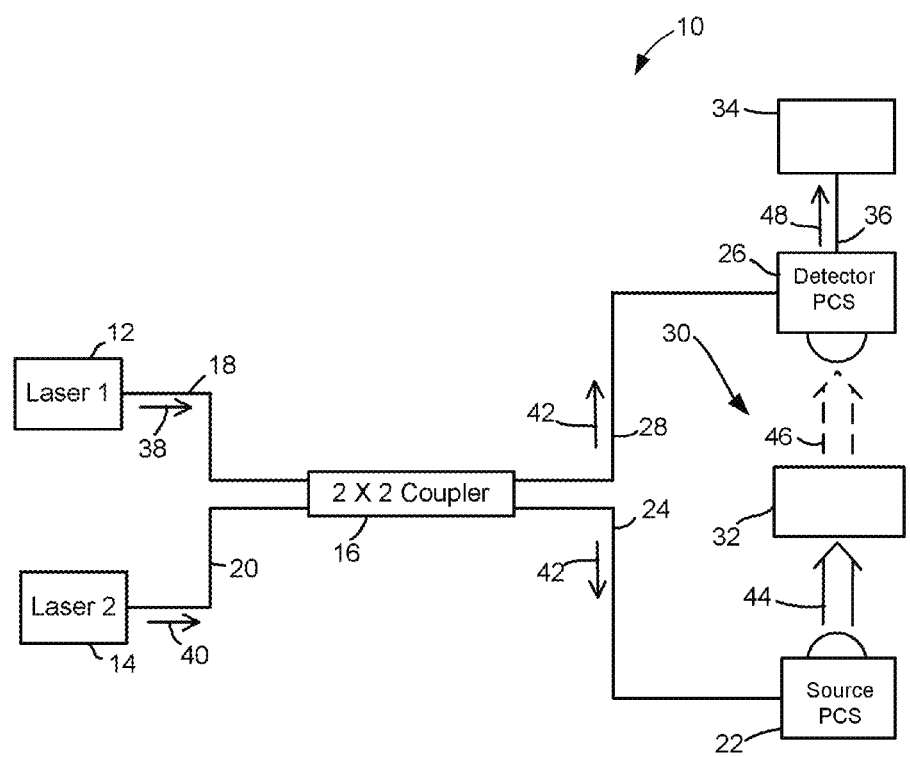
FIG. 1 is a block diagram illustrating an embodiment of a simplified terahertz spectrometer without phase modulation and phase offset control.

Attention is now directed to the Figures wherein like items may refer to like components throughout the various views. FIG. 1 is a diagrammatic representation of a simplified terahertz system 10 which can be employed for terahertz radiation production and detection. Terahertz system 10 has been presented for purposes of providing a framework for the discussion of Applicant's recognitions in the context of problems which can arise in prior art terahertz frequency spectrometers. Terahertz system 10 includes a first laser 12 and a second laser 14 which are optically coupled to a 2×2 optical coupler 16 through optical fibers 18 and 20, respectively. The 2×2 coupler is optically coupled to a source photoconductive switch (PCS) 22 through an optical fiber 24 and to a detector PCS 26 through an optical fiber 28. The source and detector PCSs are positioned relative to a sampling region 30 in which a material 32 is positioned. The detector PCS is electrically connected to a detection circuit 34 through an electrical cable 36.

The first and second lasers can be semiconductor diode lasers, such as distributed feedback (DFB) lasers, that each produce laser light at a different single frequency from one another at any given time. The first laser can generate a first laser light 38 and a second laser can generate a second laser light 40. The frequency of the light from either one or both of the lasers can be controlled by changing the temperature of one or both of the lasers; and the difference between the laser light frequencies is in the terahertz frequency range. A range of terahertz frequencies can be produced over a time period by changing the difference between the laser light frequencies over the time period.

The 2×2 optical coupler receives laser light 38 and 40 from the lasers and optically outputs a combined light 42 that is made up laser light 38 and 40. Of course, the frequency of the light from the respective lasers is not modified. The source and detector PCSs can be low-temperature grown GaAs photoconductive switches. The source and detector PCSs receive combined light 42 and optically photo mixes the two laser light frequencies to produce and detect terahertz radiation, respectively. The source PCS includes a biased antenna (not shown), and the mixing of the two frequencies of light on the biased antenna of the source PCS generates a free space terahertz frequency radiation beam 44. The mixing of the two frequencies of light on the detector PCS, which is unbiased, provides a local oscillator required for homodyne detection. The terahertz radiation generated by the source PCS can be swept through a range of frequencies over a time period by changing the frequency difference between the laser light frequencies over the time period. The radiation beam is directed from the source PCS through a sampling region 30 in which the beam interacts with material 32 to produce a characterized radiation beam 46 which is received by the detector PCS. Characterized radiation beam 46 contains a terahertz frequency spectral characteristic which is related to characteristic frequencies that are at least partially absorbed when the terahertz radiation is swept through the range of frequencies.

The detector PCS detects the characterized radiation beam and produces a characterized terahertz signal which is mixed with the local oscillator internally in the detector PCS to produce a detector signal 48. Detector signal 48 is supplied to the detection circuit 34 over electrical cable 36. The detection circuit receives the detector signal and produces a response that can be characterized by a graph 60 (FIG. 2) of power data 62 for the terahertz frequencies applied to the material. As shown in graph 60, the terahertz frequencies applied to the material in the present embodiment are in a range from about 200 GHz to just over 1.5 THz. Graph 60 also shows noise 64 in the system. Power data 62 contains terahertz frequency spectral characteristic information of the material. However, Applicants recognize that the characteristics of the material as shown in power data 62 are largely indistinguishable because the detector signal contains a null signal component 66.

Figure 2:
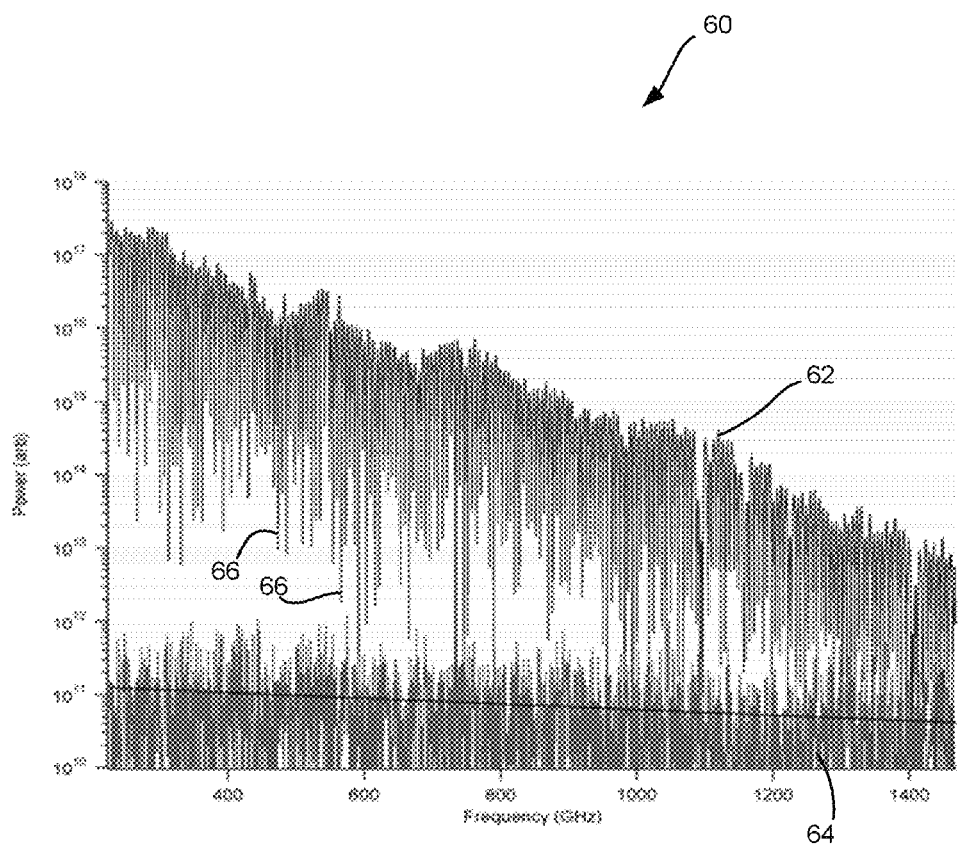
FIG. 2 is a graph of a power curve which can result from using the spectrometer shown in FIG. 1.

Referring again to FIG. 1, terahertz system 10 is fully coherent, meaning that the local oscillator in the detector PCS used in the homodyne detection is generated by the same frequency source as the radiation beam from the source PCS. However, the path length of the light and terahertz radiation through the sampling region is different than the path length of the light to the detector PCS where the local oscillator is generated. Also, the terahertz radiation can be subjected to dispersion between the source and detector PCSs, including dispersion caused by the free space atmosphere as well as the material in the sampling region. The dispersion and path length difference can create a phase difference between the characterized terahertz signal, resulting from the characterized terahertz radiation beam and the local oscillator that is frequency dependent. As a result, when the terahertz frequency is generated and swept through the frequency range of about 200 GHz to just over 1.5 THz, as shown in FIG. 2, the characterized terahertz signal and the local oscillator periodically move between being completely in phase with one another to completely out of phase with one another. When these signals are completely in phase, the phase offset between the signals is zero degrees and when these signals are completely out of phase the phase offset between the signals is 180 degrees. When the offset is zero degrees, the signals constructively interfere, which results in a strong signal, and when the offset is 180 degrees, the signals destructively interfere, which results in the nulls, which are weak signals at those points. The series of nulls can be referred to as an interference pattern and the distance between the nulls is indicative of the frequency of the interference pattern. In the embodiment shown in FIG. 2, the interference pattern has a frequency of roughly 4 GHz.

The existence of the interference pattern can negatively impact system performance. In order to avoid aliasing, the frequency resolution employed by the system should fully resolve the interference pattern regardless of the width of the characteristic of the material in the sampling region. For example, the explosive composition RDX has a characteristic with a width of over 100 GHz. However, if a system with the fringe spacing shown in FIG. 2 were employed to characterize a sample of RDX, a resolution of 0.5 GHz is required to properly record the interference pattern. Otherwise, aliasing occurs and the characteristic RDX absorption feature cannot be discerned. Also, a technique in which a background scan is recorded prior to introducing the sample into the sampling region and then is subtracted from the scan of the material cannot be used because the introduction of the material into the sampling region changes the effective path length and introduces dispersion which can cause the nulls of the interference pattern to shift.

Figure 3:
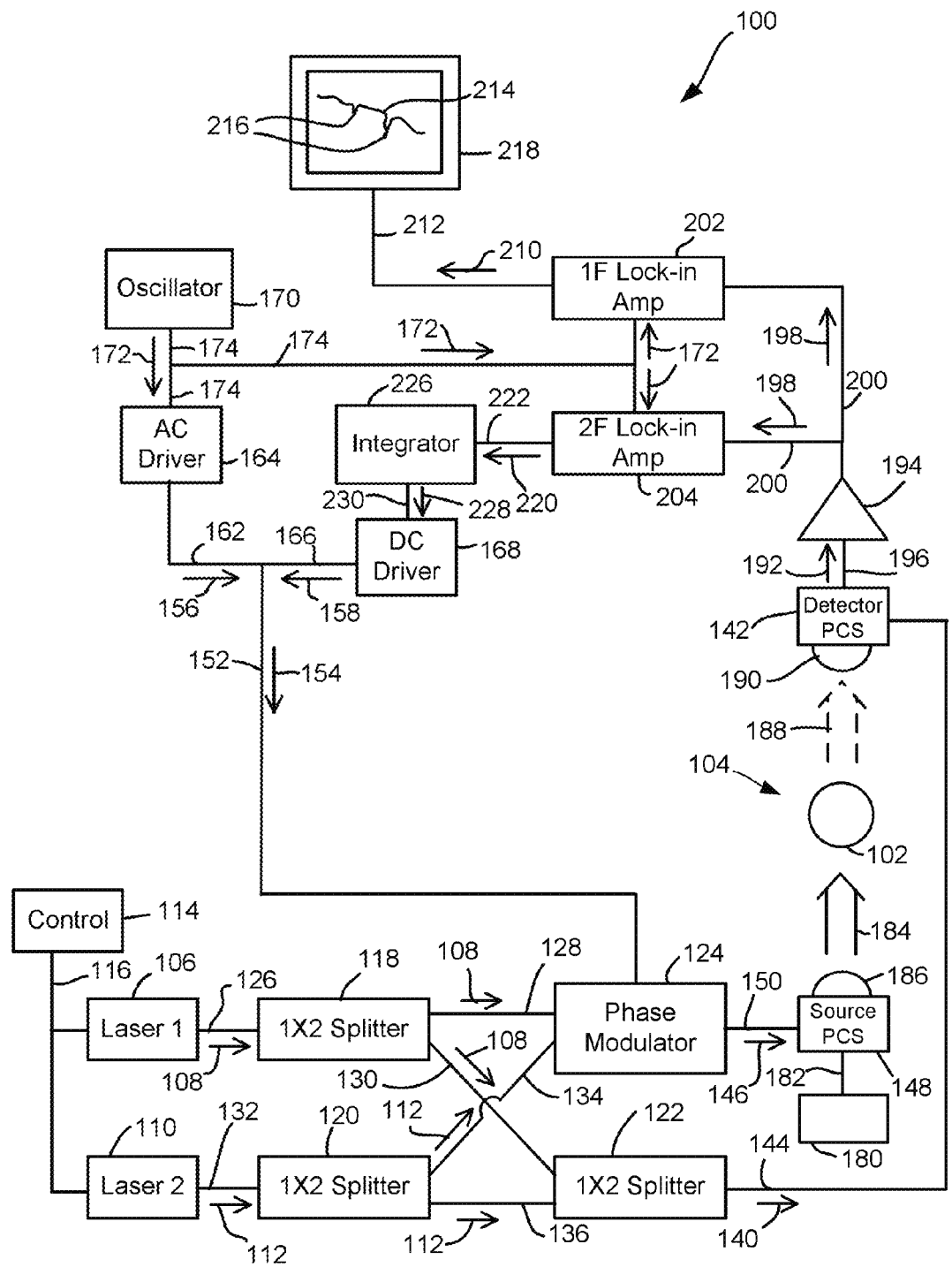
FIG. 3 is a diagrammatic illustration of an embodiment of a terahertz spectrometer with a phase modulator and phase offset control in accordance with the present disclosure.

Referring now to FIG. 3, an embodiment of a terahertz system 100 is shown which can be utilized for identifying a terahertz frequency spectral characteristic of a material 102 in a sampling region 104. Unlike system 10, terahertz system 100 can reduce and/or eliminate the interference pattern nulls so that the terahertz frequency characteristic of the material can be determined without the negative impact on the system performance introduced by the interference pattern nulls.

Terahertz system 100 includes a first laser 106 that produces a first laser light 108 and a second laser 110 that produces a second laser light 112. The first and second lasers can be single frequency semiconductor diode lasers, such as for example, distributed feedback (DFB) lasers, that each produce laser light at a different, single frequency (at least from a practical standpoint) from one another at any given time. The frequency of the light from either one or both of the lasers can be controlled, such as for example, by changing the temperature of the laser, using a controller 114 which can be connected to one or both of the lasers through a control line 116. The difference between the frequencies of first laser light 108 and second laser light 112 can be controlled within a range from gigahertz to terahertz, which can be referred to herein generally as a terahertz frequency range. The terahertz frequency range can include those terahertz frequencies that can be used to identify the material in the sampling region. One or both of the lasers can be controlled such that the difference between the frequencies of the laser lights can be swept over all or part of the terahertz frequency range over a time period.

Terahertz system 100 also includes 1×2 optical splitters 118, 120 and 122 and a phase modulator 124. Splitter 118 receives first laser light 108 from the first laser through an optical fiber 126 and splits the first laser light at least approximately equally to supply the first laser light to phase modulator 124 and splitter 122 through optical fibers 128 and 130, respectively. Splitter 120 receives second laser light 112 from the second laser through an optical fiber 132 and splits the second laser light at least approximately equally to supply the second laser light to phase modulator 124 and splitter 122 through optical fibers 134 and 136, respectively.

Optical splitter 122 receives first laser light 108 from optical fiber 130 and second laser light 112 from fiber 136 and combines the light to supply a combined laser light 140 without frequency modification. Splitter 122 is optically connected to a detector PCS 142 through an optical fiber 144 over which combined laser light 140 is carried from splitter 122 to detector PCS 142.

Phase modulator 124 receives first laser light 108 from optical fiber 128 and second laser light 112 from fiber 134 and combines the light into a combined laser light 146 having the same frequencies as combined laser light 140. Phase modulator 124 is optically connected to a source PCS 148 through an optical fiber 150 which carries combined laser light 146 from the phase modulator to the source PCS. Although phase modulator 124 is shown optically connected to the source PCS and splitter 122 is shown optically connected to the detector PCS, in other embodiments the phase modulator can be optically connected to the detector PCS and splitter 122 can be optically connected to the source PCS. Phase modulator 124 receives a phase modulator control signal 154, for controlling the phase modulator, over a control signal line 152.

Phase modulator control signal 154 includes both a capacitively coupled AC signal component 156 and a resistively coupled DC signal component 158. The AC signal component controls the phase modulator to periodically modulate the phase difference between the first and second laser lights at a modulating frequency. The DC signal component is utilized by the phase modulator to control a phase offset between the first and second laser lights relative to which the phase is periodically modulated, as will be discussed in further detail.

AC signal component 156 is supplied through an AC signal component conductor 162 by an AC driver 164 to control signal line 152. DC signal component 158 is supplied through a DC signal component conductor 166 by a DC driver 168 to control signal line 152. A reference oscillator 170 generates a low frequency reference waveform 172 and supplies the reference waveform to the AC driver through a reference waveform conductor 174. The low frequency reference waveform can have a frequency of a few kilohertz to a few megahertz. The reference oscillator can originate the waveform as a square wave and the reference oscillator can include a waveform shaping circuit that converts the square wave into either a triangle wave or a sign wave that has slower transitions between maximum and minimum values than the square wave. Any suitable waveform can be used. The AC driver circuit receives the reference waveform and produces the AC signal component; the AC driver circuit can adjust an output voltage swing of the AC signal component, as will be discussed in further detail.

Source PCS 148 is connected to a DC bias source 180 through a DC bias line 182 which supplies a fixed DC bias to the source PCS. Combined laser light 146, received by the source PCS, creates a beat pattern which produces a combined optical amplitude that varies at a rate given by the difference between the two optical frequencies in the combined laser light. This varying optical amplitude causes a resistance of the source PCS to vary at the difference frequency rate and the DC bias causes a corresponding current signal through the varying resistance. Since the difference frequency is in the terahertz range, the current signal is also in the terahertz range and the terahertz current signal from the source PCS flows through a connected spiral antenna (not shown) and generates a free space terahertz electromagnetic radiation beam 184. The phase of electromagnetic radiation beam 184 depends upon the relative phase of the two laser lights at a point where the photoconductive switch is illuminated. Therefore, phase modulating and controlling the phase offset optically using phase modulator 124 also phase modulates and controls the phase offset of electromagnetic radiation beam 184. The terahertz electromagnetic radiation beam is collimated by terahertz optics 186 which directs the terahertz radiation beam toward the detector PCS, through sampling region 104. The terahertz radiation beam interacts with material that is positioned in the sampling region, such as material 102, and a characterized terahertz radiation 188 is produced which includes terahertz frequency spectral characteristics that are related to the material. For example, as terahertz radiation beam 184 is swept through the range of terahertz frequencies, certain characteristic terahertz frequencies, which depend on the type of material, can be absorbed by the material to some extent. Other terahertz frequencies of terahertz radiation beam 184, which are not absorbed by the material, can pass through the material from the source PCS to the detector PCS without any substantial loss of power. These characteristic terahertz frequencies are spectral characteristics which can be used for identifying a compound material and/or materials in the compound material.

Detector PCS 142 receives combined laser light 140 from splitter 122 to create a beat pattern in the detector PCS. The beat pattern produces a resistance in the detector PCS that serves as a homodyne local oscillator that varies at the same terahertz rate as the resistance in the source PCS. The resistance in the detector PCS varies at the same terahertz rate as the varying resistance in the source PCS because the combined laser light 140 contains the same two light frequencies as combined laser light 146.

Detector PCS 142 includes terahertz optics 190 which focus characterized terahertz radiation 188 onto a spiral antenna (not shown) of the detector PCS. For example, a spiral antenna can receive the characterized terahertz radiation and produce a characterized terahertz voltage signal across the varying resistance in the detector PCS. The characterized terahertz voltage signal across the varying resistance produces a detector signal current 192 that is the product of the characterized terahertz voltage signal and the terahertz varying resistance. Because the resistance is modulated by the optical field of the two laser lights illuminating the detector switch which are also used for generating the terahertz radiation beam, the result is a homodyne mixing of the locally-generated terahertz signal (the terahertz varying resistance which serves as the local oscillator) and the incoming characterized terahertz signal in the antenna from the characterized radiation. The homodyne mixing of the locally generated terahertz signal in the detector and the characterized terahertz signal eliminates the terahertz frequency content.

Detector signal 192 includes low frequency content based on the reference waveform frequency that is produced by the phase modulation. The low frequency content includes a first harmonic signal component and can include a second harmonic signal component depending on the phase offset, as will be discussed in further detail. Detector signal 192 also includes a characterized signal component that is related to the terahertz frequency spectral characteristic of the material. The detector signal is supplied by the detector PCS to an amplifier 194 via a detector signal conductor 196. Amplifier 194 can be a low noise amplifier that amplifies detector signal 192 and produces an amplified detector signal 198 which is supplied to a signal conductor 200. Detector signal 198 is supplied to a 1F lock-in amplifier 202 and a 2F lock-in amplifier 204. The lock-in amplifiers are connected to reference waveform conductor 174 to receive reference waveform 172 from reference oscillator 170.

The 1F lock-in amplifier receives detector signal 198 and uses reference waveform 172 as an input to extract the characterized signal component from the detector signal. The 1F lock-in amplifier provides an amplitude measurement of the first harmonic of the detector signal. This lock-in amplifier is referred to as a 1F lock-in amplifier because the reference input to the lock-in amplifier is at the same frequency as the signal that it is detecting. The output of the 1F lock-in amplifier is a characterized signal 210 that is supplied on a signal line 212 which can be processed and/or displayed on a display device 216, for example, as a characterized power curve 214.

The 2F lock-in amplifier also receives detector signal 198 and reference waveform 172 as a reference input. Lock-in amplifier 204 is referred to as a 2F lock-in amplifier because this amplifier provides an amplitude measurement of the second harmonic of the detector signal. The 2F lock-in amplifier produces an error signal 220 on an error signal conductor 222 that is a magnitude of a second harmonic of the reference waveform frequency in detector signal 198. Error signal conductor 222 is connected to an integrator 226 that applies a bias and a biased error signal 228 is supplied by the integrator over an error signal conductor 230 to DC driver 168 which provides the DC signal component of the phase modulator control signal to the phase modulator.

Figure 4A:
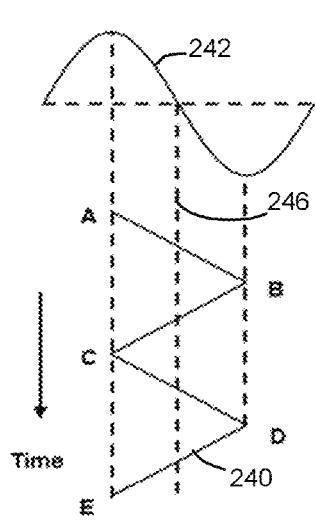
FIG. 4a is an illustration of a phase modulation waveform at a zero degree phase offset that can be used in the spectrometer of FIG. 3.
Figure 4B:
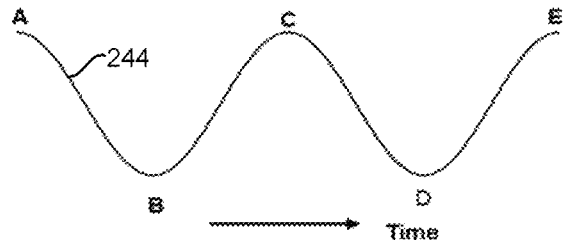

Referring now to FIG. 4a and FIG. 4b in conjunction with FIG. 3, in an embodiment, phase modulator control signal 154 can include an AC signal component in the form of a triangle wave 240. AC driver 164 can adjust the output voltage swing of the triangle wave to produce a peak-to-peak optical phase shift of 180 degrees which produces the terahertz electromagnetic radiation with a periodic phase shift of 180 degrees peak-to-peak. A one cycle sinusoidal waveform 242 is shown that represents the phase relationship between the reference terahertz signal (the local terahertz oscillator in the detector PCS) and the characterized terahertz signal resulting from the detection of the characterized terahertz electromagnetic radiation received by the detector PCS as the two signals are mixed in the detector PCS. When the fringes (FIG. 2) are at a maximum the terahertz signals are in phase and when the fringes at a minimum the terahertz signals are 180 degrees out of phase. The optical phase modulator is biased using DC signal component 158 of phase modulator control signal 154. When the phase modulator is biased at zero degrees offset 246, which can also be referred to as quadrature, the triangle wave drives the phase shift to be equally balanced between the maximum or minimum of a fringe. When the phase modulator is biased at zero degrees offset, detector signal 192 includes a first harmonic sine wave 244 (FIG. 4b) that is at the same frequency as reference waveform 172 and does not include a second harmonic.

Figure 5A:
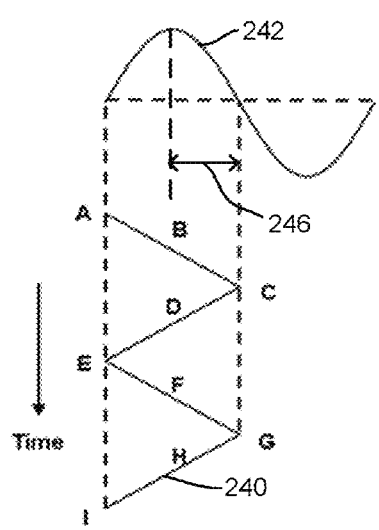
FIG. 5a is an illustration of a phase modulation waveform at a non-zero degree phase offset.
Figure 5B:
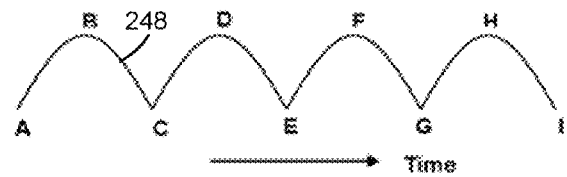

Referring now to FIG. 5a and FIG. 5b in conjunction with FIGS. 3, 4a and 4b, when phase offset 246 is not set at zero degrees, detector signal 192 from the detector PCS includes a waveform 248 (FIG. 5b) that can have a first harmonic component and a second harmonic component. In the embodiment shown in FIGS. 5a and 5b, the optical phase modulation is centered on a fringe maximum which is a negative 90 degree phase offset and waveform 248 exhibits a period of twice the modulation frequency such that the signal is positive going. In an embodiment in which the optical phase modulation is centered on a fringe minimum, which is a positive 90 degree phase offset, the waveform exhibits a period of twice the modulation frequency and the signal is negative going instead of positive going. That is, the signal is a mirror image of the signal shown in FIG. 5b. Although shown in FIGS. 5a and 5b in the context of a 90 degree phase offset, whenever there is a non-zero phase offset between the characterized terahertz signal and the local terahertz oscillator, the detector signal will contain nulls in characterized signal 210 from the 1F lock-in amplifier caused by the second harmonic component in the detector signal. Because of this, when the 2F lock-in amplifier detects the second harmonic, the 2F lock-in amplifier produces the error signal. The latter is used to create the DC signal component of control signal 154 which shifts the offset to reduce or eliminate the second harmonic and thereby reduce or eliminate the nulls. By continuously adjusting the phase modulator bias voltage so that the characterized terahertz signal and the local oscillator in the detector PCS continually maintain an optimal, in-phase, alignment regardless of the material in the sampling region, the nulls can be eliminated (at least from a practical standpoint) so that the characterized power curve can be clearly produced.

Figure 6:
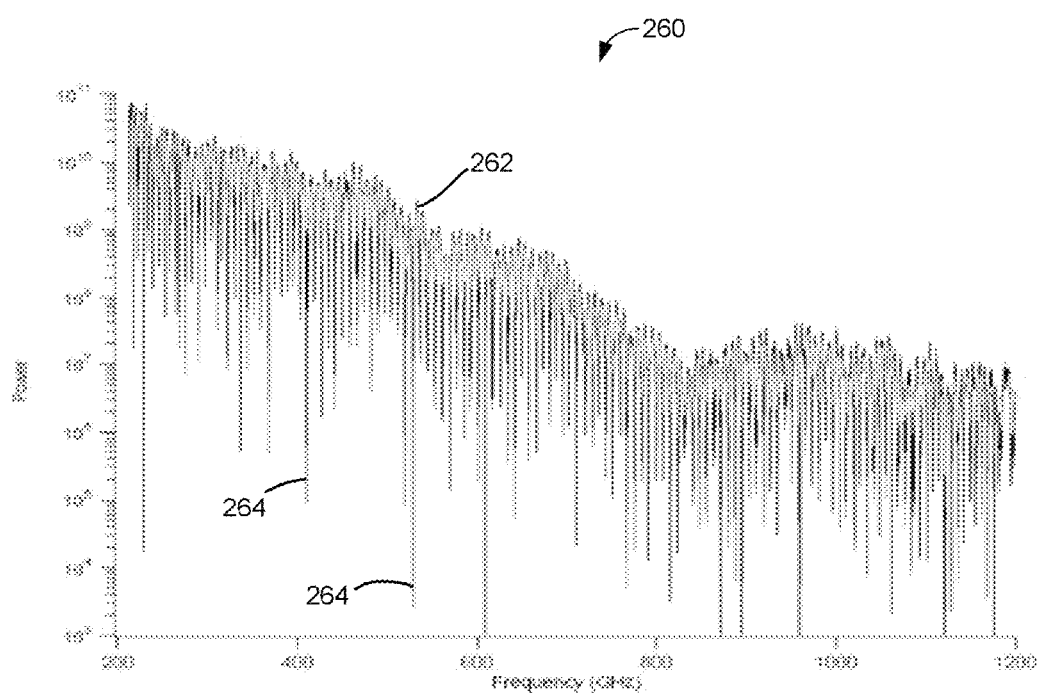
FIG. 6 is an illustration of a power curve that can be produced when the phase offset is not controlled.

Referring now to FIG. 6, an example of an embodiment of a graph 260 (for illustrative purposes) shows an example of a power curve 262 that can be produced when the phase offset between the characterized terahertz signal and the local oscillator is not controlled. As the characterized terahertz signal and local oscillator are swept through the range of terahertz frequencies causing the phase offset to change. Applicants recognize that nulls 264 are produced which obscure the spectral characteristics of the material.

Figure 7:
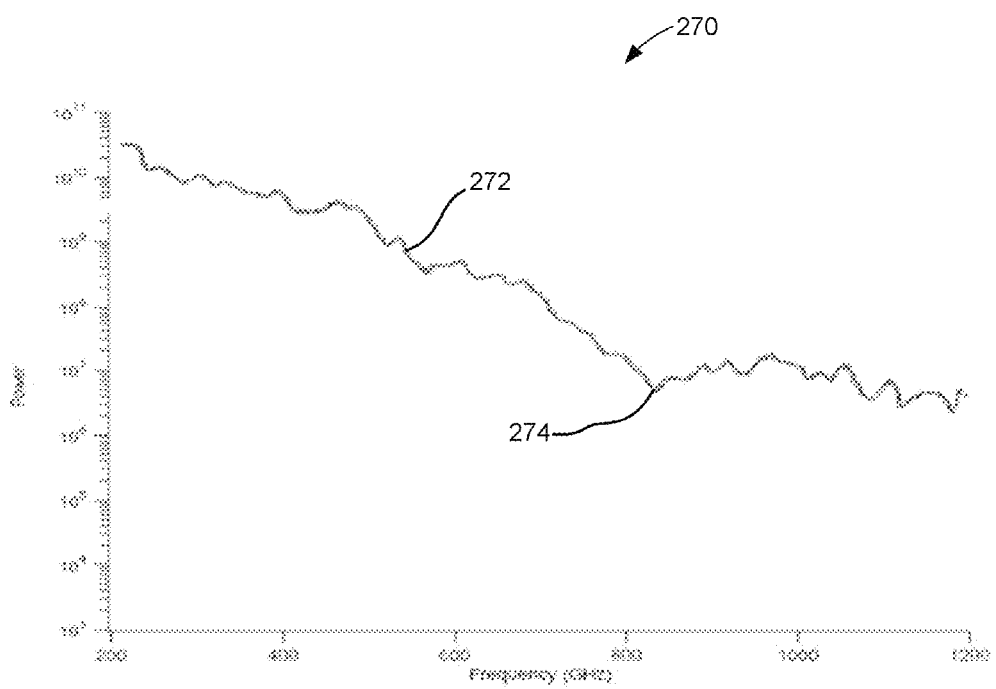
FIG. 7 is an illustration of a characterized power curve which can be produced using the terahertz system shown in FIG. 3.

Referring now to FIG. 7, a graph 270 illustrates an embodiment of a characterized power curve 272 which can be produced using terahertz system 100. Power curve 272 can include a terahertz frequency spectral characteristic 274 of the material in the sampling region which can be used for identifying the material. In this embodiment, the terahertz electromagnetic radiation and local oscillator are swept through a frequency range from about 200 GHz to about 1200 GHz; and the terahertz characteristic of interest occurs at approximately 820 GHz. In this embodiment, the phase offset is controlled using the error signal produced by the detection of the second harmonic while the frequency of the terahertz radiation and local oscillator are swept through the terahertz the frequency range, thereby eliminating the second harmonic and allowing the extraction of the characterized signal component from the first harmonic using the 1F lock-in amplifier.

Figure 8:
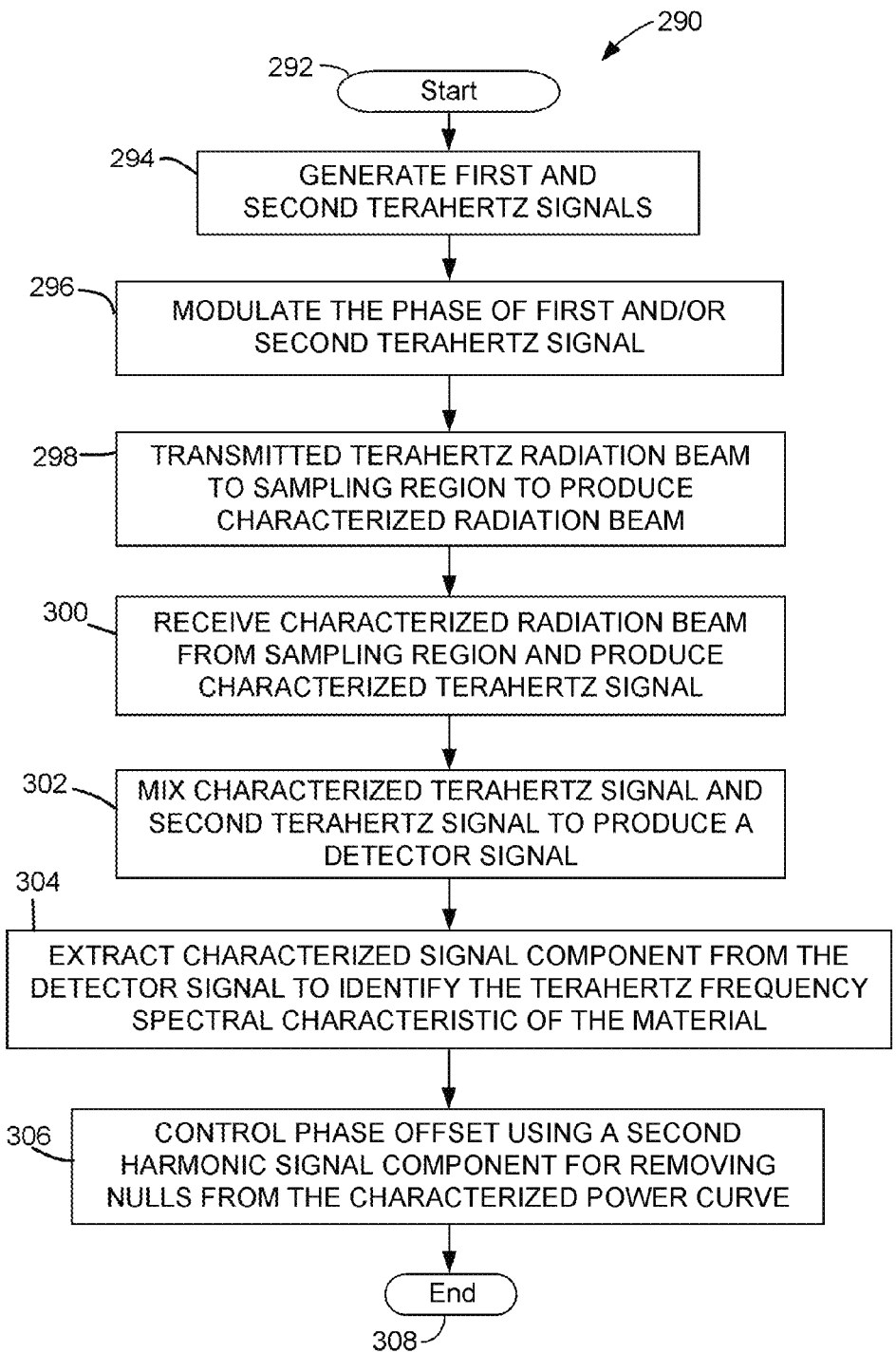
FIG. 8 is a method for identifying a terahertz frequency spectral characteristic of a material in a sampling region.

Referring now to FIG. 8, a method 290 is shown for identifying a terahertz frequency spectral characteristic of a material in a sampling region. Method 290 begins at 292 and proceeds to 294 where a first terahertz signal and a second terahertz signal are generated. The method then proceeds to 296 where the phase of at least one of the first and second terahertz signals is modulated relative to a phase offset in a periodic manner at a modulating frequency. The method then proceeds to 298 where a terahertz electromagnetic radiation beam is transmitted that is based on the first terahertz signal. The radiation beam is transmitted to the sampling region such that a characterized terahertz radiation is produced by the interaction of the terahertz radiation beam with the material in the sampling region. The characterized terahertz radiation includes a terahertz frequency spectral characteristic that is related to the material. Method 290 then proceeds to 300 where the characterized terahertz radiation is received from the sampling region and a characterized terahertz signal is produced responsive to the received radiation. The method then proceeds to 302 where the characterized terahertz signal and the second terahertz signal are mixed to produce a detector signal that includes a characterized signal component related to the characteristic of the material. The detector signal also includes a first harmonic signal component at a first harmonic of the modulating frequency resulting from the phase modulation; and a second harmonic signal component at a second harmonic of the modulating frequency. The second harmonic component is a result, at least in part, of the phase offset between the phases of the characterized terahertz signal and the second terahertz signal. Method 290 then proceeds to 304 where the characterized signal component is extracted from the detector signal to identify the terahertz frequency spectral characteristic of the material in the sampling region. The extracted characterized signal component defines a characterized power curve that includes nulls which are reduced power levels at certain frequencies related to the second harmonic signal component of the detector signal. The method then proceeds to 306 where the phase offset is controlled using the second harmonic signal component such that the nulls are, at least in part, removed from the characterized power curve. Method 290 then proceeds to 308 where the method ends.

Various embodiments of systems and techniques are disclosed herein in which terahertz frequency spectral characteristics of a material can be identified using second harmonics to produce an error signal for eliminating interference pattern nulls. These techniques can be used for identifying materials that have terahertz frequency characteristic signatures through materials that are transparent at terahertz frequencies, and for other purposes. The systems and techniques described herein are non-destructive to the material being tested so a material can be tested multiple times and the material can be used for its intended purpose even after testing. Applicants submit that apparatus, systems and methods according to the present disclosure provide sweeping and heretofore unseen benefits that are not recognized by prior art.

While a number of exemplary aspects and embodiments have been discussed above, those of skill in the art will recognize certain modifications, permutations, additions and sub-combinations thereof. It is therefore intended that the following appended claims and claims hereafter introduced are interpreted to include all such modifications, permutations, additions and sub-combinations as are within their true spirit and scope.

What is claimed is:

1. A terahertz frequency spectrometer for identifying a terahertz frequency spectral characteristic of a material in a sampling region, comprising:

a terahertz source for generating a first terahertz signal and transmitting a terahertz electromagnetic radiation beam, based on the first terahertz signal, to the sampling region such that a characterized terahertz radiation is produced by an interaction of the terahertz electromagnetic radiation beam with the material in the sampling region, the characterized terahertz radiation including the terahertz frequency spectral characteristic related to the material;

a terahertz detector for generating a second terahertz signal and for receiving the characterized terahertz electromagnetic radiation from the sampling region and producing a characterized terahertz signal responsive to the received radiation, the terahertz detector mixing the characterized terahertz signal and the second terahertz signal to produce a characterized detector signal;

a phase modulator for applying a phase modulation in a way that modulates the phase of at least one of the first terahertz signal and second terahertz signal in a periodic manner at a modulating frequency, wherein the phase modulator modulates the phase relative to a phase offset that is a difference between the phases of the characterized terahertz signal and the second terahertz signal, and wherein the characterized detector signal includes a characterized signal component related to the characteristic of the material, and a first harmonic signal component at a first harmonic of the modulating frequency resulting from the phase modulation, and a second harmonic signal component at a second harmonic of the modulating frequency resulting, at least in part, from the phase offset;

a characteristic detector for extracting the characterized signal component from the detector signal to identify the terahertz frequency spectral characteristic of the material in the sampling region, the extracted characterized signal component defining a characterized power curve that includes nulls which are reduced power levels at certain frequencies related to the second harmonic signal component of the detector signal; and a phase offset controller for controlling the phase offset using the second harmonic signal component such that the nulls are, at least in part, removed from the characterized power curve.

2. The terahertz frequency spectrometer as defined in claim 1, further comprising:

a first laser for generating a first laser light; and a second laser for generating a second laser light, and wherein the terahertz source is configured to receive the first and second laser lights and to generate the first terahertz signal based on the first and second laser lights, and the terahertz detector is configured to receive the first and second laser lights and to generate the second terahertz signal based on the first and second laser lights at the same frequency as the first terahertz signal, and wherein the phase modulator is an optical phase modulator that is configured to apply the phase modulation to modulate the phase difference between the first and second laser lights to modulate the phase of the terahertz signal.

3. The terahertz frequency spectrometer as defined in claim 2, further comprising:

a laser frequency controller for controlling the frequency of at least one of the first and second laser lights such that the frequency of the first and second terahertz signals changes over a time period.

4. The terahertz frequency spectrometer as defined in claim 3, wherein the laser frequency controller is configured to control the laser light frequency to sweep the frequency of the terahertz signal through a range of frequencies during the time period.

5. The terahertz frequency spectrometer as defined in claim 2, wherein the phase offset controller is an optical phase offset controller that is configured to control the phase of at least one of the first and second laser lights to control the phase offset between the characterized terahertz signal and the second terahertz signal.

6. The terahertz frequency spectrometer as defined in claim 1, further comprising:

a lock in amplifier for producing a phase offset control signal based on the second harmonic signal component of the detector signal, and wherein the phase offset controller is configured to receive the phase offset control signal from the lock in amplifier and to control the phase offset based on the phase offset control signal to remove the nulls from the characterized power curve.

7. The terahertz frequency spectrometer as defined in claim 6, wherein the characteristic detector is a first harmonic lock in amplifier that detects the first harmonic frequency for extracting the characterized signal component from the detector signal.

8. The terahertz frequency spectrometer as defined in claim 7, wherein the phase offset controller is configured to control the phase offset to reduce the second harmonic signal component to thereby reduce the nulls in the detector signal.

9. The terahertz frequency spectrometer as defined in claim 1, wherein the phase offset controller controls the phase offset to maintain the phase offset at approximately zero degrees.

10. The terahertz frequency spectrometer as defined in claim 1, wherein the phase modulator periodically modulates the phase of the terahertz signal 180 degrees.

11. The terahertz frequency spectrometer as defined in claim 10, wherein the phase modulator periodically modulates the phase of the terahertz signal between −90 degrees and +90 degrees relative to the phase offset.

12. A terahertz frequency spectrometer for identifying a terahertz frequency spectral characteristic of a material in a sampling region, comprising:

a terahertz beam source for generating a terahertz beam that passes through the sampling region thereby producing a characterized terahertz radiation that is influenced by the material;

a local oscillator generator for generating a terahertz local oscillator signal at the same frequency as the terahertz beam;

a phase modulator for applying a phase modulation in a way that modulates the phase of at least one of the terahertz beam and terahertz local oscillator signal based on a modulation input;

a mixer for producing an output signal based on the characterized terahertz radiation and the terahertz local oscillator signal that can exhibit a pattern of nulls resulting from the phase modulation and which includes a first harmonic that characterizes the terahertz spectral characteristic of the sample; and a lock in amplifier for detecting a second harmonic of the output signal to produce an error signal for driving the modulation input based on the error signal to at least reduce the nulls.

\* \* \* \* \*